United States Patent [19]

Harris et al.

[11] 4,243,671

[45] Jan. 6, 1981

[54] INHIBITION OF THROMBOXANE SYNTHETASE FORMATION AND ARACHIDONIC ACID-INDUCED PLATELET AGGREGATION AND BRONCHOCONSTRICTION

[75] Inventors: Don N. Harris, Somerset; Marie B. Phillips, Skillman; Roland Greenberg, Princeton, all of N.J.

[73] Assignee: E. R. Squibb & Sons, Inc., Princeton, N.J.

[21] Appl. No.: 30,420

[22] Filed: Apr. 16, 1979

[51] Int. Cl.$^3$ .......................................... A61K 31/415
[52] U.S. Cl. .............................................. 424/273 R
[58] Field of Search ................................... 424/273 R

[56] References Cited

PUBLICATIONS

Tai et al. Biochem. and Biophys. Res. Commun., 80: 236–242 (1978).
Yoshimoto et al. Prostaglandins, 16, No. 4, 529–540 (1978).
Nijkamp et al. Europ. J. Pharmacoc., 44; 179–186 (1977).
Chemical Abstracts 83: 157710t (1975).
Moncada et al., Prostaglandins 13, No. 4; 611–618 (1977).

*Primary Examiner*—Leonard Schenkman
*Attorney, Agent, or Firm*—Lawrence S. Levinson; Burton Rodney

[57] ABSTRACT

1-(3-Phenyl-2-propenyl)-1H-imidazole, and its hydrochloride salt have been found to be potent inhibitor of thromboxane synthetase and therefore an inhibitor of arachidonic acid-induced platelet aggregation and bronchoconstriction.

7 Claims, No Drawings

INHIBITION OF THROMBOXANE SYNTHETASE FORMATION AND ARACHIDONIC ACID-INDUCED PLATELET AGGREGATION AND BRONCHOCONSTRICTION

BACKGROUND OF THE INVENTION

Thromboxane $A_2$ ($TxA_2$) is a potent, unstable biosynthetic product of arachidonic acid. It is a very potent platelet aggregating, vasoconstricting and bronchoconstricting agent. Inasmuch as these properties could be harmful to an organism, compounds which could inhibit thromboxane synthetase and thereby inhibit formation of thromboxane $A_2$ could be of importance. Thus, for example, imidazole has been shown to be a specific inhibitor of thromboxane synthetase. Nijkamp et al., "Diversion of Prostaglandin Endoperoxide Metabolism by Selective Inhibition of Thromboxane $A_2$ Biosynthesis in Lung, Spleen or Platelets", Europ, J. Pharmacol., 44:179–186, (1977); Moncada et al, "Imidazole: A Selective Inhibitor of Thromboxane Synthetase" (1977) Prostaglandins 13, 611–618 and Tai et al. "On the Inhibitory Potency of Imidazole and its Derivatives on Thromboxane Synthetase", Biochem. and Biophys. Res. Commun. 80:236–242 (1978) disclose that 2-, 4- and 6-substituted imidazoles are inactive while 1-substituted imidazoles wherein the substituent is alkyl, benzyl and 2-isopropylphenyl are inhibitors of thromboxane synthetase formation.

Yoshimoto et al, "Selective Inhibition of Prostaglandin Endoperoxide Thromboxane Isomerase by 1-Carboxyalkylimidazoles", (1978), Prostaglandins, 16, 529–540 disclose that 1-carboxyalkylimidazoles and 1-alkylimidazoles are inhibitors of the conversion of prostaglandin $H_2$ to thromboxane $B_2$.

Selective inhibitors of thromboxane synthetase have potential in the prevention of myocardial ischemia, angina pectoris, myocardial infarction, stroke and transient ischemic attacks, diabetes, intravascular inflammation, asthma, anaphylactic shock, atheroschlerosis, endotoxin shock, certain viral conditions, and systemic and pulmonary hypertension.

DESCRIPTION OF THE INVENTION

It has now been found that 1-(3-phenyl-2-propenyl)-1H-imidazole

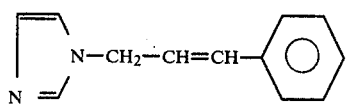

and its acid addition salts such as the hydrochloride salt, are effective in inhibiting thromboxane synthetase and arachidonic acid-induced platelet aggregation and bronchoconstriction.

The inhibition of thromboxane synthetase according to the present invention is obtained by contacting blood platelets with a concentration of from about 1 to about 1000 $\mu$M of 1-(3-phenyl-2-propenyl)-1H-imidazole or its hydrochloride salt or other pharmaceutically acceptable acid addition salt.

The 1-(3-phenyl-2-propenyl)-1H-imidazole compound of formula I is a known compound and is disclosed by Baggaley et al, "Hypolipidemic Imidazoles", J. Med. Chem., 1975, 18, 833–836, Example 39.

The compound of formula I may be employed in the free form or in the form of its acid addition salts. The salts thereof can be converted into the free compound in a known manner such as by reaction with a basic agent. The free base which may be obtained can be converted into pharmaceutically acceptable acid addition salts by reaction with a variety of acids. Acids useful for preparing these acid addition salts include, inter alia, inorganic acids, such as the hydrohalic acids (e.g., hydrochloric and hydrobromic acid), sulfuric acid, nitric acid, and phosphoric acid, and organic acids such as maleic, fumaric, tartaric, citric, acetic, benzoic, 2-acetoxybenzoic, salicyclic, succinic, nicotinic, methanesulfonic or cyclohexanesulfamic.

The compound of formula I including its pharmaceutically acceptable salts has exhibited the ability to inhibit the action of thromboxane synthetase and arachidonic acid induced platelet aggregation and bronchoconstriction according to the general procedures described by Nijkamp et al, supra, Born, G. V. R., "Aggregation of Blood Platelets by Adenosine Diphosphate and Its Reversal," Nature 194:927–929, 1962 and Amdur and Mead, "Mechanics of Respiration in Unanesthetized Guinea Pigs," Amer. J. Physiol. 192, 364–368 (1958) as modified by Giles et al, "The Bronchodilator and Cardiac Stimulant Effects of Th 1165a, Salbutamol, and Isoproterenol," J. Pharmacol. Exp. Ther. 186, 472–481 (1973). Thus, the compound of formula I may be useful in the treatment or prevention of myocardial ischemia, angina pectoris, myocardial infarction, stroke and transient ischemic attacks, intravascular inflammation, asthma, anaphylactic shock, atherosclerosis, and endotoxin shock.

The compound of formula I including its pharmaceutically acceptable salts can be administered orally or parenterally to various mammalian species in amounts ranging from about 1 to about 100 mg/kg/day divided into one or more doses for the pharmaceutical purpose set forth above. The compounds are formulated with an inert carrier according to conventional pharmaceutical practice, for example in the form of tablets, capsules, or an injectable solution.

The following Examples demonstrate the activity of the 1-(3-phenyl-2-propenyl)-1H-imidazole, hydrochloride (1:1).

EXAMPLE 1

Inhibition of Arachidonic Acid Induced Platelet Aggregation

Venous blood is collected from the antecubital vein of human volunteers who are drug free for at least one week. The blood is collected by gravity into plastic transfer bags containing 0.38% sodium citrate as the anticoagulant. Platelet-rich plasma (PRP) is prepared by centrifuging the citrated blood at 200×g for 10 min at 25° C. Platelet-poor plasma (PPP) is obtained by centrifuging the PRP at 2500×g for 30 min at 25° C.

Platelet aggregation is studied photometrically (Boron, Nature 194:927–929, 1962) using a Chronolog aggregometer connected to a linear recorder. The test compound is dissolved in methanol and preincubated with PRP for 2.5 minutes at 37° C. Arachidonic acid (800 $\mu$M) dissolved in 0.1 M Tris-HCl buffer, pH 8.5, is then added and the optical transmission recorded for at least 3 minutes. The rate of increase in optical transmission, which is a measure of the initial velocity of aggregation, is measured by determining the slope of the steepest part of the curve.

The test compound is found to be 100% effective in inhibiting platelet aggregation at the screening concentration of 1 mM. and has an $I_{50}$ (concentration to achieve 50% inhibition) of 30 μM.

EXAMPLE 2

Inhibition of Thromboxane Synthetase

Thromboxane synthetase is prepared from fresh PRP according to the procedure of Nijkamp et al, supra. Briefly, a platelet pellet is washed in physiological saline, and the platelets lysed by a combination of freeze-thaw cycles and homogenizations. This platelet membrane suspension is divided into small aliquots and stored at −70° C. until used.

Thromboxane synthetase activity is determined by incubating the platelet preparation with $^{14}C$-arachidonic acid in a reaction mixture containing epinephrine, reduced glutathione, and Tris-HCl buffer, pH 7.5.

Thromboxane synthetase activity is determined in the presence of the test compound dissolved in methanol, or of the methanol control. The reaction is carried out for 3-5 minutes at 37° C. and stopped by the addition of 2N HCl. In some instances, aliquots of the reaction mixtures are spotted directly on Quantum thin layer plates for thin layer chromatography of reaction mixture components. In other experiments, the lipids in the reaction mixture are extracted into ethyl acetate. After the ethyl acetate is taken to dryness, the lipid residue is dissolved in ethanol and aliquots spotted on the thin layer plates. In either instance, the plates are developed using chloroform:methanol:acetic acid (90:5:5) as solvent system. The isolated thromboxane-$B_2$ is scraped from the plate, put into scintillation counting vials containing 10 ml of a dioxane-base scintillation counting mixture. The radioactivity that migrates in the area of thromboxane-$B_2$ is then determined by liquid scintillation spectrometry.

The test compound is found to be a potent inhibitor of thromboxane synthetase activity. It inhibits 83% at 1000 μM and has an $I_{50}$ of 30 μM.

EXAMPLE 3

Inhibition of Arachidonic Acid-induced Broncho-constriction in the Anesthetized Guinea Pig Male guinea pigs weighing 480–520 g are anesthetized with urethane (1.5 g/kg, i.p.). Spontaneous respiration is arrested with succinylchloline chloride (1.5 mg/kg, i.p.). The guinea pigs are artificially ventilated with a Palmer respiration pump through a tracheal cannula at a rate of 72 strokes/min and a stroke volume of 3 ml.

Pulmonary resistance and dynamic compliance are determined by the method described by Amdur and Mead, "Mechanics of Respiration in Unanesthetized Guinea Pigs", Amer. J. Physiol. 192, 364–368, as modified by Giles et al. (1973), "The Bronchodilator and Cardiac Stimulant Effects of Th 1165A, Salbutamol, and Isoproterenol", J. Pharmacol. Exp. Ther. 186, 472–481. Respiratory flow is measured with a Fleisch pneumotachograph (No. 000) and a Validyne (MP 45) differential pressure transducer. Transpulmonary pressure is determined by monitoring the difference between pressure in the external end of a tracheal cannula and the pressure in the pleural cavity by means of a Validyne MP 45 differential pressure transducer. The flow and pressure signals are fed into an on-line analog Pulmonary Mechanics Computer (Buxco Electronics, Inc.) which provides calculation of pulmonary resistance and dynamic compliance. The computer output of flow, pressure, volume, resistance and dynamic compliance are recorded on a Brush 260 recorder. Blood pressure is measured from a carotid artery with a Statham P23Db transducer and heart rate is derived from the pulse pressure. Both blood pressure and heart rate are recorded with the Buxco pulmonary mechanics computer. All parameters are digitalized by a Data Logger, Model DL-12 Buxco electronics and recorded on a Texas Instrument silent 700 ASR printer.

Arachidonic acid (AA) (0.25 mg/kg i.v.) is administered to groups of 4–5 guinea pigs 15 minutes before and 3 and 10 minutes after the administration of the test compound (0.1, 0.3 and 1.0 mg/kg i.v.). The administration of AA causes substantial increases in pulmonary resistance (R) and decrease in dynamic compliance (C) of 70% and 50% respectively. The prior administration of the test compound (0.1–1.0 mg/kg, i.v.) causes a significant dose dependent decrease in the AA-induced changes in R and C. The inhibitory effect of the test compound lasts for less than 10 minutes. The administration of the test compound (0.1, 0.3 and 1.0 mg/kg) in the above experiments causes profound hypertension of long duration up to 30 minutes but, does not significantly alter R, C or heart rate.

In 8 additional control experiments AA (0.25 mg/kg i.v.) is administered 15 minutes before and 3 minutes after saline. There is no significant difference between the first and second bronchoconstrictor responses to AA.

Four additional experiments are done to see if the antagonistic effects of the test compound are specific for AA. Histamine (5.0 μg/kg i.v.) is administered 15 minutes before and 3 minutes after the administration of the test compound (1.0 mg/kg i.v.). Histamine caused large increases in R and decreases in C which are not altered by the administration of the test compound.

What is claimed is:

1. A method of inhibiting thromboxane synthetase activity, and thus inhibiting arachidonic acid-induced platelet aggregation and broncho-constriction, which comprises administering to the circulatory system of a mammalian host in need thereof an effective amount of 1-(3-phenyl-2-propenyl)-1H-imidazole or a pharmaceutically acceptable acid addition salt thereof.

2. The method as defined in claim 1 wherein said 1-(3-phenyl-2-propenyl)-1H-imidazole is administered in an amount within the range of from about 1 to about 100 mg/kg.

3. The method as defined in claim 1 wherein said imidazole is in the form of its hydrochloride salt.

4. A method of inhibiting arachidonic acid-induced platelet aggregation which comprises administering to a mammalian host in need thereof an effective amount of 1-(3-phenyl-2-propenyl)-1H-imidazole or a pharmaceutically acceptable acid addition salt thereof.

5. The method as defined in claim 4 wherein said imidazole is in the form of its hydrochloride salt.

6. A method of inhibiting arachidonic acid-induced bronchoconstriction associated with asthma, whch comprises administering to a mammalian host in need thereof an effect amount of 1-(3-phenyl-2-propenyl)-1H-imidazole or a pharmaceutically acceptable acid addition salt thereof.

7. The method as defined in claim 6 wherein said imidazole is in the form of its hydrochloride salt.

* * * * *